(12) United States Patent
Wnuk et al.

(10) Patent No.: US 9,355,123 B2
(45) Date of Patent: May 31, 2016

(54) FAST RECOGNITION ALGORITHM PROCESSING, SYSTEMS AND METHODS

(71) Applicant: Nant Holdings IP, LLC, Culver City, CA (US)

(72) Inventors: Kamil Wnuk, Playa Del Rey, CA (US); Bing Song, La Canada, CA (US); Matheen Siddiqui, Culver City, CA (US); David McKinnon, Culver City, CA (US); Jeremi Sudol, Los Angeles, CA (US); Patrick Soon-Shiong, Los Angeles, CA (US); Orang Dialameh, Santa Monica, CA (US)

(73) Assignee: Nant Holdings IP, LLC, Culver City, CA (US)

( * ) Notice: Subject to any disclaimer, the term of this patent is extended or adjusted under 35 U.S.C. 154(b) by 143 days.

(21) Appl. No.: 14/332,371

(22) Filed: Jul. 15, 2014

(65) Prior Publication Data

US 2015/0023602 A1    Jan. 22, 2015

Related U.S. Application Data

(60) Provisional application No. 61/856,580, filed on Jul. 19, 2013.

(51) Int. Cl.
  *G06K 9/46* (2006.01)
  *G06F 17/30* (2006.01)
  *G06K 9/00* (2006.01)

(52) U.S. Cl.
  CPC ...... *G06F 17/30247* (2013.01); *G06K 9/00671* (2013.01)

(58) Field of Classification Search
  CPC .................. G06F 17/30247; G06K 9/00671
  USPC ....................................................... 382/190
  See application file for complete search history.

(56) References Cited

U.S. PATENT DOCUMENTS

| 2011/0081048 | A1* | 4/2011 | Woo ............... G06T 7/2033 382/103 |
| 2011/0244919 | A1 | 10/2011 | Aller et al. |
| 2012/0281969 | A1* | 11/2012 | Jiang ............... G11B 27/11 386/278 |

OTHER PUBLICATIONS

Leutenegger, S. et al., "BRISK: Binary Robust Invariant Scalable Keypoints," Proceedings of the 13th IEEE International Conference on Computer Vision (ICCV) Nov. 6-13, 2011, Barcelona Spain.
(Continued)

*Primary Examiner* — Manuchehr Rahmjoo
(74) *Attorney, Agent, or Firm* — Fish & Tsang LLP

(57) ABSTRACT

Systems and methods of quickly recognizing or differentiating many objects are presented. Contemplated systems include an object model database storing recognition models associated with known modeled objects. The object identifiers can be indexed in the object model database based on recognition features derived from key frames of the modeled object. Such objects are recognized by a recognition engine at a later time. The recognition engine can construct a recognition strategy based on a current context where the recognition strategy includes rules for executing one or more recognition algorithms on a digital representation of a scene. The recognition engine can recognize an object from the object model database, and then attempt to identify key frame bundles that are contextually relevant, which can then be used to track the object or to query a content database for content information.

25 Claims, 2 Drawing Sheets

(56) References Cited

OTHER PUBLICATIONS

Alahi, A., et al., "FREAK: Fast Retina Keypoint," Ecole Polytechnique Federale le Lausanne (EPFL), Switzerland, CVPR 2012 Open Source Award Winner, CVPR 2012, Jun. 16-21, 2012, Providence, Rhode Island.

Liu, T., et al., "An Investigation of Practical Approximate Nearest Neighbor Algorithms," Carnegie-Mellon University School of Computer Science, Conference of Advances in Neural Information Processing Systems 17, Dec. 13-18, 2004, British Columbia, Canada.

"Textons" Department of Statistics and Computer Science, UCLA, downloaded from Center for Vision, Cognition, Learning and Art, University of California, Los Angeles, at: vcla.stat.ucla.edu/old/Chengen_Research/texton.htm on Jul. 26, 2013, 4 pages.

* cited by examiner

FAST RECOGNITION ALGORITHM PROCESSING, SYSTEMS AND METHODS

This application claims the benefit of priority to U.S. provisional application 61/856,580 filed on Jul. 19, 2013. U.S. provisional application 61/856,580, and all other extrinsic references referenced herein are incorporated by reference in their entirety.

FIELD OF THE INVENTION

The field of the invention is object access technologies.

BACKGROUND

The following description includes information that may be useful in understanding the present invention. It is not an admission that any of the information provided herein is prior art or relevant to the presently claimed invention, or that any publication specifically or implicitly referenced is prior art.

Consumers continue to experience an increasingly blurred distinction between real-world and on-line interactions. Consumers can now virtually interact with real-world objects through their smart phones. For example, consumers can capture an image of a movie poster via their cell phones. In response, the cell phone can construct an augmented reality interaction or game overlaid on the display of the cell phone. In fact, the Applicant has pioneered such technologies through their iD® technologies as implemented by DreamPlay™ (see URL www.polygon.com/2013/1/9/3851974/disney-dreamplay-ar-app-disney-infinity). Other technologies that attempt to offer similar experiences include the following:

Layar® (see URL www.layar.com),
Qualcomm Vuforia™ (see URL www.qualcomm.com/solutions/augmented-reality)
BlippAR.com™ (see URL www.blippar.com), and
13th Lab (see URL www.13thlab.com).

Unfortunately, such technologies are limited in scope and typically are only capable of recognizing a single type object at a time (e.g., a single toy, a single person, a single graphic image, single type of marker, etc.). Thus, a consumer must position their cell phone into a more ideal position or orientation with respect to the object of interest, then wait for their cell phone to analyze the image information before engaging content is retrieved. Ideally a consumer's digital device (e.g., cell phone, vehicle, tablet, etc.) should be able to engage with content associated with an object of interest very quickly and should be able to virtually engage with many objects at the same time. The above referenced companies fail to provide such features.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, there is still a need for methods of quickly recognizing multiple objects quickly.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

SUMMARY OF THE INVENTION

The inventive subject matter provides apparatus, systems and methods in which a device can leverage multiple types of digital processing algorithms to identify or recognize many different objects at the same time from a digital representation of a scene. One aspect of the inventive subject matter includes an apparatus (e.g., a cell phone, a game console, an appliance, a vehicle, etc.) capable of quickly recognizing or differentiating objects represented within a digital representation of a scene; a digital video, a video frame, or image for example. A mobile or portable version of an apparatus could optionally include a sensor configured to obtain sensor data in the form of the digital representation of the scene having a plurality of objects where the digital representation can include image data, video data, audio data, biometric data, or other types of digital data modalities. The apparatus further includes a recognition engine (i.e., a combination of software and hardware) coupled with the sensor and configured to recognize the objects based on information derived from the digital representation. The recognition engine can obtain access to an object model database that stores recognition models of known object models. The recognition models have object information indexed according to features derived from key frames (i.e., specific images) of known object models. The object model database can be remote to the apparatus or could be local to the apparatus, possibly even automatically constructed based on the received key frames. The recognition models represent a schema by which an object can be recognized. Thus, the recognition engine is able to recognize objects based on the recognition models within the object model database. The recognition engine can further determine a recognition strategy based on a captured digital representation of a scene where the strategy includes one or more rules that govern how the digital representation is to be analyzed via one or more algorithms. The recognition strategy could include an order in which the algorithms (e.g., SIFT, DAISY, FAST, BRISK, ASR, OCR, etc.) are executed on the digital representation. Resulting recognition features or descriptors obtained from the algorithms can then be used to identify a target modeled object in the object model database where a recognition model has been indexed according to features, which could be considered similar to the recognition features. Then, the recognition engine can identify one or more contextually relevant key frame bundle that can be used for tracking or referencing content and that is associated with the target modeled object. Content information can be retrieved, possibly via a content database, based on the content link and then rendered on the display. By determining a recognition strategy for different types of available digital processing algorithms and using key frame bundles, an apparatus having a low end processor can be configured to identify or differentiate multiple objects at a rate of at least 10 objects per second, 300 objects per second, or even faster. For example, multiple objects can be distinguished within a single frame rendering time of a video playing at a normal frame rate (e.g., 24 FPS, 30 FPS, 60 FPS, etc.).

Another aspect of the inventive subject matter includes a model recognition system including an object model database and an object model server. The object model database is configured or programmed to store object recognition models. Each object recognition model can include object information referenced by recognition features of a corresponding object that has been modeled. Example object models can include modeled 3D objects generated by a CAD system, by a 3D object scanning systems, by a game modeling system (e.g., Unity 3D, OpenGL, etc.), a procedurally generated object, or other digital modeling systems. Further the recognition features can be derived from modeled features such as polygons, vertices, edges, curves, bitmaps, textures, or other aspects of the modeled objects. Content information relating to the object models (e.g., the object, the model, object information, names, identifiers, etc.) can also be indexed according to recognition features. The object server, possibly operating as a service consumable by other computing devices, generates one or more key frames that represent recognition features associated with points of interest on the modeled objects. For example, a key frame could include an image of the modeled object from a specific pose, and can be bundled with one or more descriptors, position or orientation information, sensor intrinsics, or other information or metadata relating to the modeling of the object. The object model server can provide one or more key frames and attendant data to devices as reference recognition information. Possibly in response to a device identifying a relevant object, the engine can further submit a query to the content database where the query has been derived from a contextually identified key frame bundle. For example, the query could include image descriptors obtained from within the key frame bundle. In response, the object database returns content information related to object models. The contemplated system could be integrated within the apparatus discussed above or could offer its recognition services to other devices.

Yet another aspect of the inventive subject matter includes a method of recognizing many objects represented within a digital representation. The method can include a recognition engine receiving a digital representation of the objects. The engine is configured to or programmed to recognize the objects at a rate of at least one object per second through 1) deriving recognition features from the digital representation according to multiple processing algorithms, possibly according to an algorithm application rules set, 2) construction of one or more queries derived from key frame data, and 3) identifying the objects by searching for content information indexed according to key frame data satisfying the query. Once content is retrieved based on the search, it can be provided to a computing device. One should appreciate that such an approach enables a recognition engine to recognize objects at high rates including rates of at least 10 objects per second, more preferably at 100 objects per second, yet more preferably at 300 objects per second, or even at least 1000 objects per second. Further, one should appreciate that multiple objects can be distinguished or differentiated within a single frame of video. For example, the method can allow a recognition engine to recognize at least 10 objects from a single frame of video within the time it takes to render the frame while running at frame rate.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
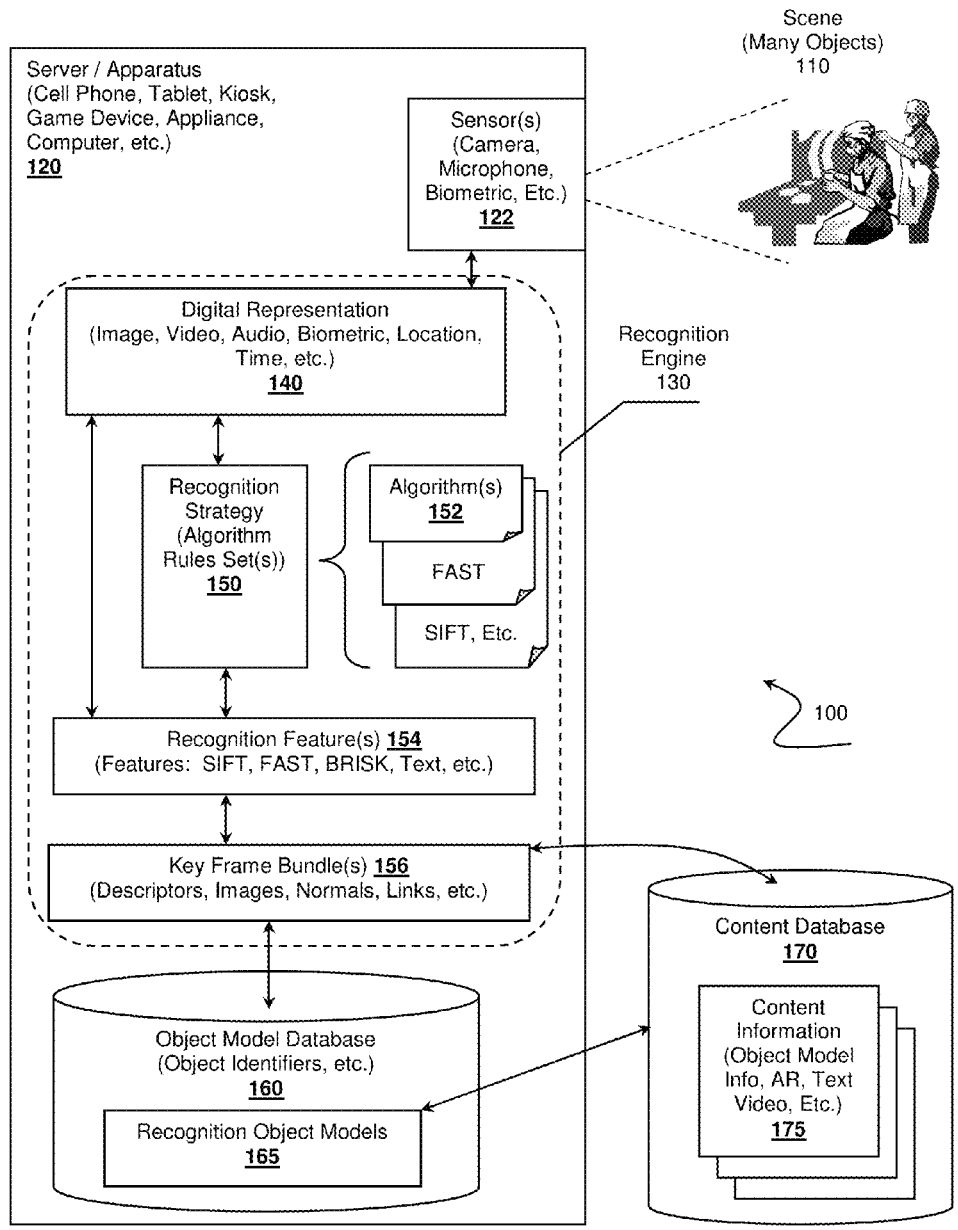
FIG. 1 presents a schematic overview of an object recognition algorithm management and processing ecosystem.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

One should appreciate that the disclosed techniques increase the efficiency with which a computing device is able to retrieve object information from a database. A computing device recognizes an object based on recognition models stored in an object model database where the recognition models can be built based on key frames relating to known objects. At test time (i.e., in the field) input signal(s) from sensor(s) on the computing device are processed by a multitude of processing algorithms according to a recognition strategy and efficiently matched to a recognition model that uniquely identifies an object, thus enabling a second query to retrieve object related content based on context-relevant key frames. The two step approach of executing a recognition strategy, then selecting contextually relevant key frame data allows for fast identification of objects and accurately providing content information back to the device.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Within the context of this document, the terms "coupled to" and "coupled with" are also used euphemistically to mean "communicatively coupled with" in a networking sense where two or more computing devices are able to send or receive data over a network.

The following discussion describes a recognition engine device digitally processing a digital representation via one or more processing algorithms. It should be appreciated that the term "algorithm" should be construed to mean a digital computing module of software stored in tangible memory and executing on one or more hardware processors. The resulting data constructs from the digital processing algorithms allows for identification of relevant content information that might be associated within one or more objects as represent by the digital representation. Such an approach can be considered as digitally recognizing one or more objects from the digital representation. For the sake of clarity, the recognition process can be considered to include the steps of 1) executing one or more algorithms on the digital representation as input in order to generate a more useful representation of the data that is more amenable to computer processing, 2) executing one or more fast matching or feature extraction algorithms on the new representation space, and 3) optionally verifying the results via one or more verification algorithms to reduce false positives. This approach quickly generates high quality matches to observed objects.

For further clarification, the applicants offer the following description of terms used in the disclosure.

A key frame can be considered a single image of an object model. Typically, a key frame is captured from a specific viewpoint or pose of the object model. For example, a toy or action figure might have six key frames; the number of key frames can be minimized based on the symmetry of the object. The six key frames for a toy could correspond to a top view, bottom view, front view, back view, left view, and right view where all the key frames are captured at a same distance from the object. It should be appreciated that an object model could have any number of practical key frames captured from many different points-of-view or captured from other varied circumstances (e.g., distance from the object, lighting conditions, simulated camera conditions, etc.). Further, the key frame could be rendered by a modeling agent (e.g., CAD, Unity 3D, game system, etc.) rather than captured by a physical camera. Key frames are used to build, or re-build, a recognition model of the object model. A key frame can also be linked with to associated model features which are visible from its specific viewpoint.

Data associated with a key frame is referenced as key frame data. Thus, the key frame data can include the image representing the key frame as well as its attendant data elements. The attendant data elements can include model features mentioned previously (e.g., a specific recognition feature, a vertex, a polygon, an object features, etc.). Further the attendant data elements could include relevant context attributes, a normal vector for the key frame, camera position or orientation relative to the object model, a lighting condition, a lighting model, or other information related to the nature of the key frame or related to the contextual applicability of the key frame.

A recognition model represents sufficient information about an object model to allow a recognition engine to determine that features derived from a digital representation of a scene are similar to features of the modeled object corresponding to the recognition model. The recognition model can be built from key frames where the key frames are analyzed via one or more algorithms, which generate features or descriptors. These features or descriptors can then be inserted into an object model database (e.g., a kd-tree, spill tree, lookup, etc.) allowing for quick matching between features observed in the field and known features of the recognition models. When a match, or nearest neighbor match, is found, the object model database can quickly return an object identifier that corresponds to the a priori modeled object. The object identifier, along with other contextual information, can be further used to retrieve relevant content information or references to relevant content information from one or more content databases. The object model database can be considered to be a collection of recognition models. Typically the recognition models are used for recognition purposes.

A key frame bundle represents a collection or bundle of information associated with an object model. The collection of information includes information sufficient for tracking recognized objects, linking to content, or other information. For example, a key frame bundle can include one or more key frames for a specific recognized object, possibly referenced via an object identifier (e.g., GUID, UUID, etc.) from the database, as well as other metadata or content information. In some embodiments, a key frame bundle can include key frame data. Therefore, the key frame bundle might include a key frame and its attendant data. However, the key frame is not required to be present in the key frame bundle.

Of particular interest is that the disclosed techniques split the data necessary for recognition and tracking. This dual set of information allows efficient transfer of only contextually necessary data as well as building contextual recognition or tracking strategies.

FIG. 1 illustrates a fast object recognition ecosystem 100 where a computing device, apparatus 120 (e.g., cell phone, server, etc.), operating as recognition engine 130 is able to quickly recognize and track many objects represented within digital representation 140 of scene 110. Once the objects are recognized, apparatus 120 can efficiently obtain corresponding content information 160, which can then be rendered for consumption by a user while the object(s) are tracked. One should appreciate that the various roles or responsibilities of the disclosed systems can be distributed among suitably equipped computing device elements of ecosystem 100. For example, in the example shown the various features of the inventive subject matter can be housed within a mobile device (e.g., a cell phone, tablet, game device, vehicle, etc.) operating as apparatus 120. Still, one should appreciate that the fast recognition system could operate as a cloud-based service possibly on a server distal from a cell phone or other sensor platform. In such an embodiment, the server can offer its recognition services as a Platform-as-a-Service (PaaS), Software-as-a-Service (SaaS), Infrastructure-as-a-Service (IaaS), Recognition-as-a-Service (RaaS), or other types of services, possibly offered as a for-fee service. Still further, the disclosed infrastructure could be deployed within a security system or closed circuit camera system, perhaps within an operating room of a hospital.

The disclosed recognition techniques achieve speed on recognition through the use of object model database 160. Object model database 160 stores one or more object recognition models 165 of known modeled objects. Recognition models 165 are constructed based on key frames generated with models of known objects. It is considered more economical to provide a few key frames for a modeled object rather than providing a full model as the key frames consume much less memory relative to a complete digital model. For example, apparatus 120 could analyze the key frames using an implementation of SIFT. The resulting descriptors can be inserted into a tree structure (i.e., object model database 160) where the tree structure forms recognition model 165 for the specific object to which the key frames are associated. Multiple recognition models 165 can be present within object model database 160. Object model database 160 can be accessed locally as shown or could be remote from apparatus 120.

Efficient object tracking and content retrieval is achieved through the use of key frame bundles 156. Key frame bundles 156 represent packages of information relating to known modeled objects where each bundle could include key frames amongst other contextual information or metadata. For example, key frame bundle 156 can include a small thumbnail key frame image of an object model (e.g., a 32×32 pixel image, a 64×64 pixel image, etc.) representing a particular point-of-view of the object. Recognition engine 130 processes the thumbnail image according to algorithms 152 to extract object recognition features 154 by which the object could be tracked. Additional information in key frame bundles 156 can also include content link, normal vectors of the key frames, augmented reality content, context attributes, or other types of data. In some embodiments, the content links from key frame bundles 156 reference content information 175 located in content database 170. It should be appreciated that key frame bundles 156 can include additional context information as discussed further below. Thus, recognition engine 130 is able to contextually track recognized objects as well as contextually retrieve content for the recognized objects.

In some embodiments as shown, a system can include one or more of object model databases 160 storing recognition models 165 associated with known or previously ingestion modeled objects. The ingestion process is described more fully with respect to FIG. 2. The modeled objects could be digitally modeled real-world objects or digitally rendered virtual objects. Recognition object models 165, as referenced early, represent the schema by which a known object is recognized, possibly via a tree. Each recognition object model 165, preferably includes a reference to an object identifier (e.g., name, UUID, GUID, etc.) that references a corresponding known object. The object identifier can be used to obtain one or more of key frame bundle 156, which could include links (e.g., URL, URI, network address, digital object identifier, etc.) to content information 175 possibly located in content database 170.

Content information 175 can comprise a wide variety of information that relates to the digital modeled objects. Examples of content information 175 can include object information, perhaps additional object identifiers (e.g., names, UUID, GUIDs, etc.), data objects, object pose data, image data, video data, audio data, augmented reality data, mask data (e.g., green screen, etc.), social media data, product data, multi-media data, text data, object data, object model data, game data, news data or other data relating to known objects. Object model database 170 is populated based on ingestion of known objects by analyzing digital representations of the known objects, more preferably through digital modeling of known objects.

In some embodiments, object model database 160 includes a complete object database storing all recognition models 165 of known or ingestion modeled objects. Such a complete database would likely best reside on a server having a large data storage capacity. The recognition models 165 can be combined as a single tree or could be clustered into groups of contextually relevant trees. In other embodiments where recognition engine 130 is disposed on a cell phone, object model database 160 could be a reduced subset of recognition model 165 relative to all known modeled objects. For example, a cell phone could build object model database 160 based on contextually relevant key frames as mentioned previously. Thus, object model database 160 can be considered a collection of relevant known models. Object model database 160 can be considered to house models of multiple known objects, giving rise to the ability of recognition engine 130 to recognize and track many objects at the same time based on the same digital representation 140.

Known objects can be a priori modeled using commercially available rendering packages possibly including Unity 3D, OpenGL, CAD, or other types of packages. Each object model comprises relevant or sufficient data to instantiate a digital version of the corresponding object, possibly including textures, vertices, polygons, wire frames, silhouettes, or other graphical information. Further, the object models can include non-graphical data. Non-graphical data can comprise material properties (e.g., density, stresses, strains, etc.), audio signatures, kinematic features or restraints, or other data that can be used to model the object. It should be appreciated that the object model can include object data that is commensurate with how corresponding objects in the field would be sensed, observed, or recognized. Thus, the object model can include a wide variety of data modalities, which can be combined with key frames.

To ingest an object, an object ingestion device can submit the object models to one or more digital processing algorithms 152 that extract recognition features from the object models. For example, the object ingestion device could execute an implementation of SIFT (see U.S. Pat. No. 6,711,293 to Lowe titled "Method and Apparatus for Identifying Scale Invariant Features in an Image and Use of Same for Locating an Object in an Image", filed Mar. 6, 2000) that generates SIFT descriptors as recognition features 154 from rendered images of the object models. It should be appreciated that any number of processing algorithms 152 (e.g., feature extraction, etc.) could process the object models and could generate recognition features across numerous data modalities.

In view that sensor 122 in the field will likely only be able to observe scene 110, and its objects, from a single point-of-view and that the ingestion system does not necessarily know a priori which point-of-view would be most likely to be used in the field, the object ingestion system generates a key frames from likely views; images that inherently represent recognition features 154 from many different perspectives or points-of-view to cover as many reasonable in-the-field use cases, subject to employing symmetry to reduce ingestion time. The object ingestion system further identifies modeled features of the object models, perhaps including vertices, polygons, or even other extracted recognition features (e.g., FAST). The modeled features can be considered points of interest related to the object and that provide object resolving power or tracking points. Further, such modeled features can aid in tracking or anchoring augmented reality (AR) content. At this point the ingestion device has key frames of the object model as well the modeled features.

The object ingestion system collects recognition features from key frames generated by one or more feature extraction modules operating according to algorithms 152. The ingestion system further binds the collection of recognition features from key frames to modeled features. Note that modeled features could correspond to a recognition feature; thus a key frame might be generated from a point-of-view having a normal vector that points to a recognition features (e.g., a FAST corner, SIFT descriptor location, etc.). Still, in other embodiments, the modeled features could be different from the recognition features. For example, the ingestion system can render a key frame image of the modeled object from a particular point of view (e.g., top, bottom, side, etc.), perhaps taking into account symmetry information. The key frame could also be captured from a point of view that is correlated with a particular modeled feature, say a detected corner (e.g., FAST corner, Harris corner), a person's eye, or other modeled feature.

The ingestion device or other device can use the key frames to build object model database 160. As referenced earlier the key frame could include a snap shot of the modeled object where, in the field, recognition engine 130 could re-derive the necessary recognition features 154 associated with the key frame by analyzing the key frame with corresponding algorithms 152. Thus, the key frame could be considered a compact representation of all possible relevant recognition features 154. In some embodiments, the ingestion device can construct object model database 165 and send it to apparatus 120. In other embodiments, the key frames along with any additional attendant data can be sent to apparatus 120, perhaps packaged in a suitable format such as XML or JSON over a network possibly via HTTP. Apparatus 120 can then build object model database 160 from the key frames.

Key frames can also be packaged with other information to aid in recognition processing. The additional data can include metadata about the key frame, recognition features or descriptors, content links (e.g., URLs, network addresses, etc.), normal vectors of key frames, camera attributes, estimated focal length, lighting condition information, database indices, context attributes, or other information derivable from the object models. In some scenarios, the key frames could also be bound with key frame bundles 156.

Key frames can be generated for numerous poses, positions, orientations, scales, relative locations, or other parameter of the modeled objects. Content information 175 related to the modeled objects can then be indexed into the content database 170 based on the key frame data for later retrieval as discussed above as well as further below.

The benefit of this approach is that the system "understands" a priori the exact position, orientation, or other configurations of each modeled feature or each contextually relevant modeled object, and can bind recognition features 154 directly to the modeled points on the modeled object. Thus, the system can be considered to "know" all possible views of the object and the context when the views are relevant. The term "recognition feature" is used euphemistically to mean members of a result set generated from processing algorithms 152 individually or collectively executed on digital representation 140. For example, the results of executing a SIFT-based algorithm results in one or more image recognition features 154 (e.g., SIFT descriptors), which would be considered recognition features.

From the perspective of a device or apparatus 120 (e.g., a cell phone, a tablet, a kiosk, an appliance, a vehicle, a game console, etc.) operating as recognition engine 130 in the field, apparatus 120 can, optionally, include at least one sensor 122 configured to obtain digital representation 140 of a plurality of objects in a scene 110. Example sensors 122 can include GPS, hall probes, cameras, RFID reader, near field radios, microphones, biometric sensors, touch screens, accelerometers, magnetometers, gyroscopes, spectrometers, strain or stress gauges, pulse oximeters, seismometer, galvanometers, Radar, LIDAR, infra red sensor, flow sensor, anemometer, Geiger counter, scintillator, barometer, piezoelectric sensor, or other types of sensors. In view that the sensors 122 can cover a broad spectrum of data acquisition devices one should appreciate digital representation 140 can comprise a broad spectrum of data modalities and could include one or more of the following types of data: image data, text data, audio data, video data, biometric data, game data, shopping or product data, weather data, or other types of data. The discussion herein presents the inventive subject matter from the perspective of image or video data for clarity purposes only without limiting the scope of the inventive subject matter. One should appreciate that the inventive subject matter is considered to include leveraging the disclosed techniques to quickly recognize objects across many different data modalities.

Digital representation 140 can also include multi-dimensional data beyond modalities. For example, in some embodiment, sensor 122 can be configured to acquire 3D video, which could be considered a 4D representation (e.g., 2D images plus depth of field plus time). Example sensors that can provide such information include Primesense® sensors, LeapMotion® or Microsoft® Kinect® sensors. In such scenarios, algorithms 152 can operate on digital representation 140 to derive features such as shape, scale, or other higher dimensional information. These higher dimensional features can be used for recognition purposes as well as determine context. Thus, the disclosed approach would be able to differentiate between a picture of an automobile and an actual automobile.

Digital representation 140 provides at least two sources of information. First, digital representation 140 can be leveraged by recognition engine 130 to determine a context in which apparatus 120 finds itself. The context represents a data structure having context attributes derived from digital representation 140. The context could include location information, ambient audio information, user profile information, heading information, or other types of attributes. The context attributes and their values can adhere to a common namespace with respect to the context information associated with other elements of the system; key frames, key frame data; key frame bundles 156, content information 175, or other elements. Such context information can be quite useful when determining recognition strategy 150. Second, digital representation 140 also represents the foundational information that directly represents observed objects and from which objects can be specifically recognized or tracked via one or more of algorithms 152.

Consider an example where a consumer shops for groceries and wishes to consult additional information about available products on a store's shelves. Older technologies required a consumer to capture an image of a bar code of a product with their cell phone. A bar code reader app (e.g., Google Goggles, RedLaser, etc.) translates the image data into a bar code value, which is then used to obtain product information. A better approach is based on the Applicant's own work where a consumer captures an image of the product itself, where the cell phone app recognizes the specific product and can return product information without requiring decoding of a bar code value. In both cases, the consumer is typically required to position the camera's field of view so that the bar code or the product dominates the field of view. Further, such apps take extended periods of time to process the image data and return a result and are limited to only 2D based recognition. The Applicant's own current product offerings are based on co-owned U.S. Pat. Nos. 7,016,532; 7,477,780; 7,680,324; and 7,565,008. To continue further with the consumer shopping example, a consumer can leverage the disclosed techniques to capture an image, or other digital representation, of multiple products on the store's shelves where each product can be individually recognized very quickly and where content information related to the recognized products can be accessed quickly through effective use of contextual key frame bundles 156. Further, as the consumer moves about a store, the content information rendered for the use can be displayed in proper relation to the tracked products. The disclosed approach is considered superior because it provides information for many objects quickly and reduces the latency between the consumer engaging with the product and the consumer engaging with the returned content information. Latency is reduced by contextually reducing the search space or search time for known objects and through construction of a contextually relevant search strategy 150.

Apparatus 120, is configured or programmed as a recognition engine 130, can recognize the objects quickly by determining recognition strategy 150 based on digital representation 140 or other contextual information. Recognition strategy 150 can include one or more algorithm application rules sets that govern how digital representation 140 should be processed by feature extraction algorithms 152 in order to recognize or track objects represented in digital representation 140. It should be appreciated that each recognition strategy 140 represents one or more computing modules having software instructions that are stored in a non-transitory computer readable memory. The algorithm application rules sets represent computer commands by which recognition engine 130 should execute feature extraction algorithms 152 on digital representation 140.

Recognition strategy 150 could comprise a set of a priori defined set of strategies or strategic packages of code. For example, in some embodiments, apparatus 120 could be provisioned with numerous, different recognition strategies 140 where each strategy can be selected based on contextual attributes derived from digital representation 140, perhaps stored as a look-up table. Example strategies might include algorithm application rules sets that comprise prioritized ordering of algorithms 152, cost-based (e.g., time, battery life, etc.) ordering of algorithms 152, parallel processing instructions, applicable algorithms, non-applicable algorithms, or other rules sets. In other embodiments, recognition strategy 150 could be instantiated by recognition engine 130 based on the context attributes derived from digital representation 140. Consider a scenario where image data and audio data is available, but the audio data is noisy. Recognition engine 140 can employ a strategy where the image data is processed first over audio data because the image data would be considered as offering more accurate results over the audio data.

Each rules set can include pointers or other references to functions, perhaps function pointers, that implement one or more of algorithms 152 (e.g., feature extraction, descriptor detection, tracking, etc.). Further, each rules set also have data elements presenting conditions or requirements (e.g., timing, order of execution, starting points, etc.) related to the corresponding algorithms. The conditions can comprise contextual attributes (e.g., location, time, etc.). For example, digital representation 140 could include video data. The recognition engine 130 could determine that SIFT analysis (e.g., identify scale invariant features) or FAST (e.g., corner detection) should be executed before curve, edge, or line detection analysis. Further, the device's GPS coordinates within the digital representation 140 might indicate that BRISK analysis should be executed before facial recognition algorithms because the GPS coordinates correspond to a sparsely populated wilderness area (e.g., national park, forest, desert, etc.) rather densely populated area (e.g., mall, store front, theme park, etc) where people would most likely to be present. Thus the construction of the algorithm application rules set can depend on a time, a location, an orientation, a context, a position, a user, a license agreement, a digital representation attribute, a frame rate, a hierarchy, an ontology, or other contextual parameters.

Consider a case where digital representation 140 comprises image data in a feature rich environment. One possible recognition strategy 150 could include the following algorithm application rules set. First, recognition engine 130 could use SIFT to operate on the image data with the assumption that the image data is feature rich. If there are too few features, then run an edge detector. If no meaningful result is achieved after edge detection, then run FAST to detect areas in the image data that likely represent text. Finally, OCR can be run on the text if desired. This type of rules structure might be most useful in a context where there are likely many recognizable objects, such as in a store having a priori known products on the shelf rather than nature setting. However, this strategic structure might be less relevant in a natural setting that is, in fact, feature rich but lacks text.

One should appreciate that the spectrum of processing algorithms 152 can also be quite diverse just as the data modalities of the digital representation 140 can be quite diverse. Further, algorithms can be considered to fall within different classes of algorithms, which can be used to determine recognition strategy 140. Processing algorithms 152 and their corresponding modules process digital representation 140 to generate one or more recognition features 154 such as visual features (e.g., SIFT, FAST, DAISY, FREAK, SURF, BRISK, etc.), edges (e.g. Canny), curves, contours, textures, raw pixels, quantized symbols (e.g. bar code, QR code, matrix code, etc.), audio or other temporal signatures, biometric statistics, or any statistic extracted from a possible input modality. In some embodiments, dimensional reduction techniques such as Principle Component Analysis (PCA), K-means clustering, or other clustering techniques can be applied to achieve more compact representations of recognition features 154. Fast matching of these low-level representations can be achieved through nearest neighbor approaches (e.g. kd-tree, spill-tree, etc.) within object model database 160. In the case of visual modalities, hypotheses for object poses can be obtained through a variety of schemes (e.g. Hough transform, sliding window, etc.). All of these represent interchangeable components of a recognition system, leading to a large family of possible approaches. Automatic Speech Recognition (ASR) and Optical Character Recognition (OCR) are examples of processing algorithms applied in specific domains. Note that multiple types of algorithms, for example ASR, OCR, and feature-based visual object recognition, can be integrated together to achieve improvements in recognition recall or precision via construction or recognition strategy 150. Such algorithms can be the foundation for later tracking or mapping algorithms possibly including SLAM or vSLAM as aided by information from key frame bundle 156.

Recognition engine 130 executes the processing algorithms 152 according to the algorithm application rules set as determined from recognition strategy 150. As algorithms 152 are executed on digital representation 140, recognition engine 130 collects recognition features 154 from the results. For example, executing a SIFT algorithm on an image will result in a collection of SIFT recognition features typically quantified as 128-byte descriptors; other sized descriptors are also possible including 36-bytes descriptors, etc. One should appreciate that recognition features 154 can include features (e.g., descriptors, artifacts, corners, edges, etc.) from many different algorithms, each having a specific data structure or data object format according to the implementation of algorithms 152. Recognition engine 130 can match recognition features 154 with recognition models 165 in object model database 160 to identify known objects that are most likely represented in digital representation 140. For example, SIFT descriptors can be used to search a tree structure in object model database 160 according to recognition model 165 to identify a known object identifier. In response, recognition engine 130 can use the object identifiers or other information linked to recognition models 165 to obtain contextually relevant key frame bundles 156 in support of tracking recognized objects.

In some embodiments recognition strategy 150 can alter the manner in which object model database 160 or its recognition models 165 are searched. As recognition engine 130 obtains contextual information from digital representation 130, perhaps a location or time of data, recognition engine 130 can instantiate a recognition strategy 150 that adjusts the schema of object model database 160. For example, location information could be used to deactivate one or more recognition models 165. If recognition models 165 comprise trees, the decision nodes of the trees could have their weights change or branches temporarily pruned so that resulting searches of the trees proceed more quickly or converge to contextually relevant object information. Thus, the inventive subject matter is also considered to include construction of recognition strategies 150 that modify, change, create, or otherwise manage object model database 160 or its recognition models 165.

Recognition features 154 used for indexing object model database 160 could be arranged according to different techniques to accelerate identification of object identifiers and then key frame bundles 156. For example, recognition features 154 could be arranged in a hierarchical list, arranged into one or more clusters of recognition features, or other structures. Consider an image with 10 or more objects and a substantially uniform background. The image can be analyzed via modules that implement the processing algorithms SIFT, edge detection, and FAST which would result in three sets of corresponding recognition features 154, one from each algorithm. Once recognition features 154 are extracted with these feature extraction algorithms they are quickly matched against features appearing in one, two, three, or possibly all recognition models 165 within databases 160. Clusters of recognition features 154 that match to features derived from specific key frames are then identified within each modality via algorithms such as the Hough transform to quickly provide a rough hypothesis for matched key frame location within the test image (e.g., digital representation 140).

Recognition engine 130 can then use the generated object identifiers among other information available to identify which of key frame bundles 156 are most relevant to the current digital representation. Key frame bundles 156 that are associated with the object identifier can be further filters. For example, each of the available or otherwise contextually active key frame bundles 156 related to the identified object can include one or more descriptors in the same descriptor space as the generated recognition features 154. In some embodiments, the descriptor space is based on SIFT where key frame bundles 154 include one or more SIFT descriptors associated with a known modeled object and where the generated recognition features 154 include SIFT descriptors derived from the digital representation. The apparatus 120, operating as recognition engine 130, then searches key frame bundles 156 to identify which bundles related to the object have descriptors similar to the generated recognition features 154. One or more nearest neighbor algorithms can be used to identify relevant key frame bundles 156 quickly. For example, the key frame bundles 156 can also be arranged as a k-d tree or a spill tree so that recognition engine 130 simply returns key frame bundles 156 having descriptors that are nearest in value to the descriptors generated associated with recognition features 154. In view that the system knows the source image (i.e., key frame) of each matched descriptor, the system can determine how many matches came from which key frame bundles 156 and can select the key frame bundle 156 that is most appropriate for a match. Thus, the number of matched features generates a ranking of key frame bundles 156 indicating which has key frames that are most representative of an observed object allowing for fast tracking of the observed object.

Beyond contextually determining the nature of algorithm application rules set, apparatus 120 can also inform a recognition service of the device's contextual state (e.g., current state, previous state, or possible predicted or future state). The recognition service operating as recognition engine 130 can employ the same techniques as discussed above and then present one or more key frame bundles 156 that are contextually relevant to the device's circumstances. Such an approach is useful because only relevant bundles are made available to the device, which reduces the recognition or tracking processing time and reduces consumption of networking bandwidth by only sending relevant key frame bundles 156 if needed. It should be appreciated that pre-caching or edge caching key frame bundles 156 can be considered, metaphorically, as activating recognition or tracking spaces somewhat akin to activating relevant neurons in a brain. Further, this process can also deactivate key frame bundles 156 that would interfere with quickly processing the digital representation in a similar manner as deactivating neurons in the brain. By selectively activating contextually key frame bundles 156 or selectively deactivating contextually irrelevant key frame bundles 156, the disclosed approach quickly converges on recognized and differentiated trackable objects. Activation or deactivation could take the form of pruning key frame bundle search trees or adding branches to the search tree. In some scenario, object model database 160 could include more than the object identifier, but also include key frame bundle identifiers or identifiers of a cluster of related key frame bundles. Further, activation or deactivation can take the form of re-balancing search trees so they are more amenable to the current context. Still further, key frame bundles 156 can indicate instructions or identifiers of which tracking algorithms are most contextually relevant for the recognized objects.

Thus, apparatus 120 within the real-world or other physical environment can receive or otherwise obtain one or more key frame bundles 156 that preferably relate to a current context. For example, a person might be shopping in the sporting goods section of a local WalMart® store. Based on the GPS location of the person's cell phone or even aisle information provided by store-based location beacons (e.g., access points, SLAM, etc.), the person's cell phone can be provisioned with a collection of key frame bundles 156 associated with sporting products or brands in the specific aisle possibly before the person engages with the products. More specifically, key frame bundles 156 could be activated that enhanced edge-based recognition or tracking so that brand logos would become possibly engagement points for a consumer. It should be appreciated that key frame bundles 156 can include specific features that should be tracked for the specific pose of the observed objects. For example, key frame bundles 156 could identify one or more FAST features for tracking to observed object. Through the use of establishing recognition strategy 150, recognizing an object via recognition models 165, and filtering down to contextually relevant key frame bundles 156, apparatus 120 is able to quickly recognize object and track them in real-time.

Contextual pre-caching of key frame bundles 156 provides several advantages. One advantage of the approach is that a device's battery life is extended because the device is only required to recognize or track only relevant objects. Further, the approach provides for pre-caching key frame bundles 156 by using available sensor data while the device is not in active use. For example, based on accelerometry data or GPS data the location of the device can be determined even while the device is in a purse or pocket. Once removed from the pocket, the device can begin using fine grained location tracking (e.g., IMU, access point triangulation, etc.) to further filter or refine the list of key frame bundles 156 that are contextually relevant. Motion data captured from the device's accelerometer could be analyzed to determine if it is similar to a motion signature indicating that the device has been removed from the purse or pocket. If the motion data does match to within a confidence level, the motion signature, then the device can alter its location tracking or object recognition strategy 150.

Key frame bundles 156 can include content link information that references content information 175 located in content database 170 (e.g., locale database, search engine, big data repository, electronic medical record storage, etc.). In some embodiments, content database 170 could be implemented within object database 160. Recognition engine 130 can construct one or more content queries based on key frame data, key frame bundle content links, recognition features 154, context attributes, or other information. The query can be submitted to content database 170 and in turn content database 170 searches for content information 175 (e.g., objects, object information, product information, object models, etc.) that have been indices that satisfy the query. Content information 175 can then be provided to a device. In some embodiments, content information 175 could include an augmented reality (AR) model of a known object that can be rendered on the display of the device. The AR model can be positioned in the display relative to observed objects as the objects are tracked.

One should appreciate that the processes undertaken by recognition engine 130 can include generating recognition features 154 preferably in substantially real-time with respect to receiving digital representation 140. In embodiments where digital representation 140 comprises video data, each frame can be analyzed individually within the time it takes to render the frame. The frame that is analyzed is referred to as a "test image". Each test image could include 10, 100, or more objects to be recognized. Further, the recognition algorithm application rules set can govern the timing at which algorithm is executed on digital representation 140. For example, a first algorithm might be executed on a first test image (i.e., a video frame) of the video, the results of which are used to return a first initial rough estimate of content information 165 that might be relevant to scene 110. Moving to the second test image (i.e., a subsequent video frame), the first algorithm is executed on the second test image, while a different algorithm is executed on the first test image in parallel. The results of the different algorithms further refines the content information 175 results set from the first algorithm by seeking content information 175 that are relevant to both test images, to within similarity criteria (e.g., intersection of the two content sets, etc.). The process can then continue forward frame-by-frame and algorithm-by-algorithm until a convergent or final result set of content information 175 is made. One should appreciate that every frame of the video is not required to be a test image. Rather, a test image could be every other frame, every third frame, every fourth frame, or other frame selected according to a frequency rule set or other algorithm application rules set.

The disclosed technique provides for fast recognition and tracking algorithm application and allows processors to recognize objects very quickly. Based on the disclosed approach an Apple iPhone 5 with a dual core A6 ARM7 processor is able to recognize over 300 objects a second. For example, while processing video data a frame rate of 30 FPS, the Apple iPhone is able to identify at least 10 individual objects per frame within one frame rendering time without delay of the video stream. Thus, the disclosed system can identify at least 1 object per second, more preferably 10 objects per second, yet more preferably 100 objects per second, still more preferably at least 300 objects per second, and yet still more preferably at least 1000 objects per second. From a different perspective, the disclosed approach provides for identifying a least one identified object in digital representation 140 thought the approach described above within one sampling period of the digital representation. The sampling period could include a single image frame rendering time (e.g., no greater than $1/24^{th}$, $1/30^{th}$, $1/60^{th}$ etc. of a second), a single sample time of audio data, a single sample time of biometric data (e.g., a heartbeat, etc.), or other sample period.

As an example consider an augmented reality gaming engine on a cell phone that recognizes real-world people and buildings. As a person interacts with their surroundings, their cell phone recognizes all the nearby buildings and people through one or more recognition strategies and track the items based on contextually relevant key frame bundles, perhaps based on the device location (e.g., GPS, triangulation, beacons, etc.), time, or user profile. For example, the cell phone can build a game-specific object model database 160 from key frames generated according to the game engine. The gaming engine quickly recognizes real-world objects and uses the recognize objects to identify corresponding key frame bundles 156. The engine uses the information in key frame bundles 156 to track the objects and obtain content information 175 in the form of digital building object models, which can be overlaid on the display of the gaming engine device (e.g., cell phone, game device, etc.). The point here is that each building can have a virtual or augmented reality façade as modeled or constructed in the game. As the player interacts with the building, say damages the building; the model can be updated so that the building appears to be damaged in the augmented reality display as the buildings are tracked based on corresponding key frame bundles 156. One should appreciate that building model could be the original modeled object of the building from which key frames were originally generated. The advantages of such an approach are clear. First, recognition features map directly to features of the building models, which allows for precise rendering, placement, or tracking within the display of the device. Second, the model of the object itself can be obtained, that is recognized, very quickly because it is indexed in the object model database 160 according to features derived from the key frames. Third, all objects in the scene can be recognized in parallel rather than individually because all relevant recognition models 165 can be searched at the same time.

The object models used to construct the object model database 160 can vary in nature. In more preferred embodiments, the object models comprise at least three dimensions (e.g., width, length, depth). Still, one should appreciate that the object models can include higher dimensionality, time variance for example. Thus, the key frames derived from the object models could vary with time. For example, a person's gait could be modeled as an object over several steps. The modeled gait object can then be analyzed to generate a single key frame, by which gait related information can be retrieved. The gait's key frame data could vary over the time period over which the gait was observed. Alternatively, the gait object's key frame data could include multiple key frames where each key frame corresponds to a point in time or a short span of time. Further, the key frames could overlap each other in time, space, or other parameter.

In some embodiments, object models are constructed from real world objects. A 3D real-world object can be actively scanned (i.e., emit energy toward the object) via one or more techniques to generate a shape or polygonal model of the object. For example, an object can be scanned with a laser, LIDAR system, time-of-flight (TOF) system, structured light system that project known lighting patterns (e.g., Primesense®, Kinect®, etc.), or other technology. The results of the scan represent a 3D, possibly wireframe, model that can be managed within a 3D modeling engine (e.g., Unity 3D, OpenGL, CAD, etc.). The object can then be passively scanned (i.e., collect ambient energy, light for example) to obtain a visual appearance of the object. For example, the object can be scanned with a video camera or can be photographed with a still digital camera to obtain image data related to the object. The modeling engine can then combine the visual appearance with the polygonal model to give rise to the complete modeled object. One should note that the modeling engine has access to each surface or point of the model and has a mapping of the image data to each of the modeled points or surface. Further, each modeled feature can be bound with a normal vector indicating a relative orientation, position, or other spatial parameter. This approach allows for quick progression from recognizing object based on recognition features directly to tracking or displaying content based on modeled features.

The modeling engine uses the object model to create key frames for the modeled objects. In view that the modeling engine is aware of each modeled feature (e.g., coordinates in 3D space, normal vector, distance from camera, observed recognition features, etc.), the modeling engine can establish correlations between one or more recognition features with the modeled features. For example, the image data (e.g., a still image taken by the camera, a video frame, etc.) can be aligned with the modeled features by projecting a vector or ray from the position and orientation of the camera to one or more model features. Thus, a key frame can be bound to object model information. Then, the image data can be analyzed via one or more of feature-based algorithms (e.g., SIFT, FAST, etc.). The resulting descriptors, image data, or other recognition features 154 collectively form key frame data (e.g., key frame and associated information) that can then be bound to the modeled feature (e.g., 3D coordinate, normal vector, surface, estimated focal length, etc.). In some scenarios, the key frame data can be packaged into the key frame bundles. The procedure can then be repeated for any number of poses of the 3D object. Thus, the disclosed modeling engine can build an object-specific key frame database from which recognition engine 130 can be provisioned with contextually relevant, object-specific recognition "micro" databases. The normal vectors within each key frame aid in providing an expectation of which viewing angles provide visibilities to various object surfaces or relative recognition features 154. The key frame data can then be used to construct key frame bundles that are provided to a device for tracking or content retrieval.

In a very real sense, the object-specific key frame data represent a projection of a 3D object onto a 2D recognition surface where key frames represent the quantified data on the 2D surface. An astute reader would appreciate that the disclosed approach could be considered a holographic recognition space because desirable recognition information for a 3D object is projected on to key frames in a manner that could be consider as adapting the holographic principle for use with object recognition.

Although key frame bundles 156 can include recognition features 154 (e.g., descriptors, 3D coordinates, etc.) that enable tracking among other capabilities, in some embodiments key frame bundles 156 can include additional information beyond recognition features 154. In addition to a key frame of a corresponding modeled feature, the key frame bundle 156 could also include lighting condition information indicating how recognition features 154 or the image would change under different conditions (e.g., light intensity, light positions, light coloring, shading, shadowing, etc.). Further, the key frame bundles 156 could also include non-image related information, possibly based on mechanical properties of the modeled object (e.g., density, mass, compressive strength, ductility, shear modulus, Young's modulus, etc.). Such information has several uses. First, the information can aid in identifying corresponding key frame bundles 156 when a real-world object is handled or deformed. Second, the information can aid in augmented reality settings by allowing a device to properly model an object within a virtual setting via anchor points or other modeled features. Other properties that can be integrated within a key frame bundle 156 could include magnetic properties, optical properties, thermal properties, acoustic properties, chemical properties, electrical properties, or other properties. Thus, one aspect of the inventive subject matter includes recognizing objects based on observed non-image based object properties.

One should appreciate that content information can be indexed into content database 170 or other database according to the key frame data as well as or in lieu of recognition features 154. When similar key frame data is encountered during a recognition event, the key frame data can be used to query the appropriate content databases 170 to obtain the indexed content information 175. In view that each and every modeled feature of the modeled object could have its own key frames, one should appreciate that each and every modeled feature could be linked to different content information 170 via the key frame data. Consider a scenario where a person is shopping for an automobile. The automobile could be a priori modeled as discussed above. Rather than merely indexing a single set of content information 175 to all key frames generated from the modeled automobile, key frames generated from a front view of the automobile could be linked with information about the engine. Key frames generated from a rear view of the automobile could be linked with information about towing capacity or cargo space. Thus, each key frame could be linked with widely different content.

In view that the disclosed recognition engines 130 and apparatus 120 can be configured or programmed to recognize objects based on object models, one should appreciate that the object models can be used to construct object masks. Referring back to the example regarding an augmented reality game utilizing buildings, the object model of the building could be a rendered mask that either overlays at least a portion of the building in the game display, or overlays other items besides the building in the display. Thus, the object model returned as content information 175 could be considered a mask or an inverse mask. Further, the mask could include a green screen mask. For example, as the person interacts with animated objects in the game, the person's cell phone can use the mask of the person (e.g., a person's object model) to remove all background features and replace the background features with Chroma Key or Chroma Key Compositing (e.g., green screen data).

The green screen approach also allows for capturing green screen content in a very economical manner. In view that multiple recognized objects are known and that their models (e.g., shape, orientation, position, etc.) are known based on the key frame information, the objects could be treated as background while occluding objects could be considered foreground. Thus, digital representations of the foreground objects could be captured as new content. Further, the foreground objects could be individually analyzed or interpreted. For example, in scenarios where the foreground object is a person's hand, the gestures of the hand can be interpreted for command or control over a virtual setting (e.g., game, user interface, etc.) or for sign language.

From a server perspective, one or more servers can operate as a service providing recognition services or tracking support services. Such systems can include the object model database 160 and an object model server. As discussed above, the object model database 160 can be configured or programmed to store recognition models 165 related to known object models. Further the system can include content database 170 that includes content information 175 indexed by key frame or key frame data. In the server perspective, the object model database 170 can be quite extensive or large storing millions or more pieces of content information 175 related to the object models, possibly over a distributed database architecture spanning many individual servers (e.g., peer-to-peer, Bit torrent, etc.).

The object model server can be configured to derive recognition features 154 from digital representation 140, possibly obtained from a remote client device (e.g., cell phone, tablet, etc.). The server could alternatively or also receive the recognition features 154 from a remote device possibly through a push or pull protocol model. In some embodiments, the recognition features 154 are pushed to the server by the remote device, a cell phone for example, via one or more protocols (e.g., FTP, HTTP, email, SSH, SSL, etc.). In other embodiments the server can request the data from the device.

One should appreciate that recognition features 154 could also be constructed by the object model server itself. For example, the object model server can receive the digital representation and analyze it according to algorithms 152 to generate recognition features 154. The object model server can then use the recognition features 154 to determine which of key frame bundles 156, by way of object model database 160, are to contextually relevant to observed objects.

The server derives one or more queries from key frame bundles 156 and targeting the content database 170. The query can include one or more key frames, directly content addresses or links, partial key frames, descriptors, links, portions of the key frame bundle, or other parameters available. The reader is reminded that the content information 175 stored in the content database 170 can be indexed by numerous aspects of the key frame data. Thus, the server is able to obtain content information 175 related to at least one object model from content database 170 where the retrieved content information 175 has been indexed by key frame data (e.g., descriptors, relevant contexts, URLs, etc.). One or more pieces of content information 175 in the result set from the query can then be provided to the requesting computing device. Such an approach is considered advantageous within the context of search services, social media, on-line gaming, shopping, or other activities where many objects can be represented within the digital representation at the same time. It should also be appreciated that the sever could provide contextually relevant key frame bundles 156 to the remote device to aid in tracking observed objects.

Figure 2:
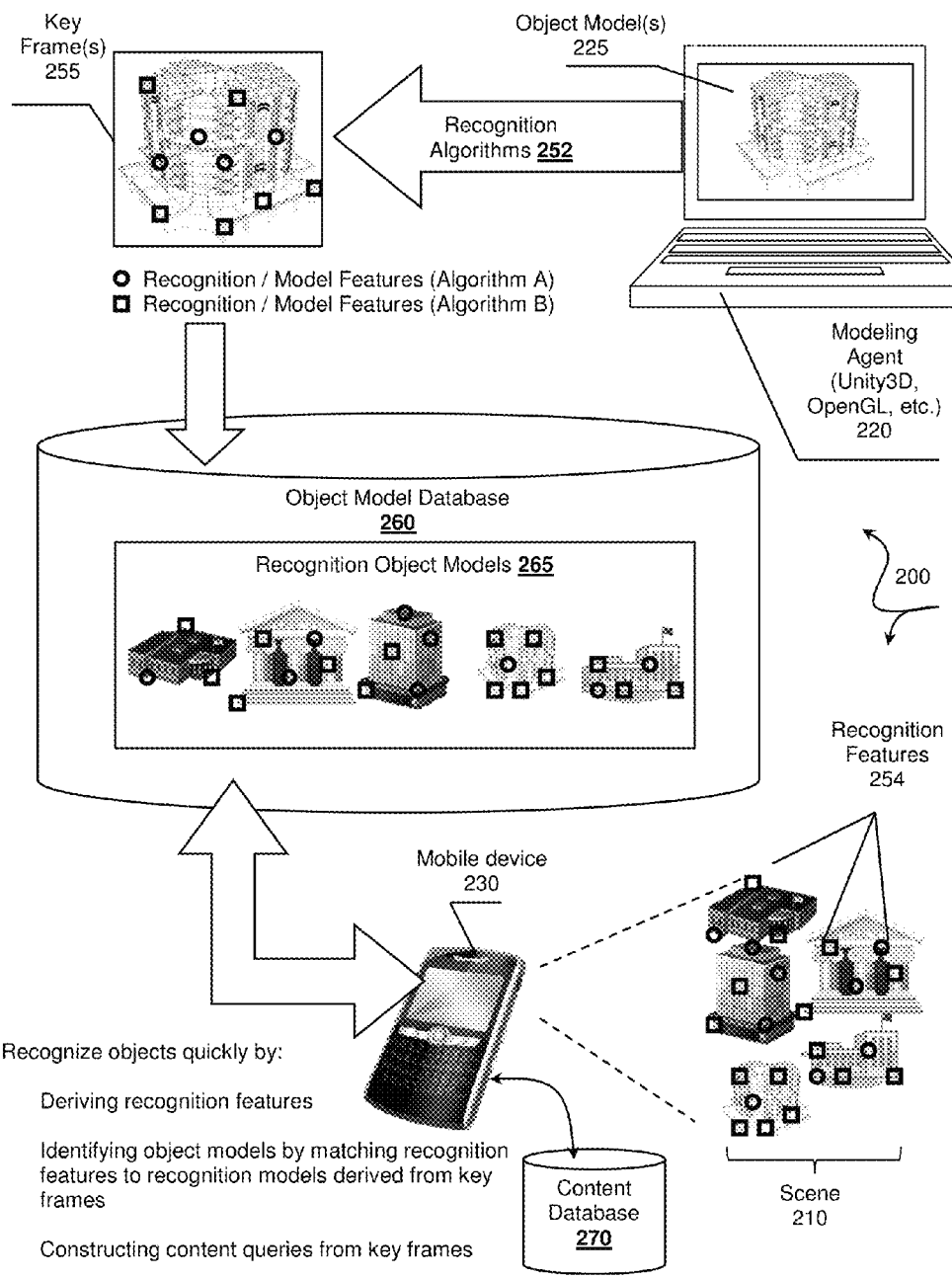
FIG. 2 illustrates an overview of a method of recognizing multiple objects.

FIG. 2 illustrates an information flow schematic that provides some clarity on a method by which a plurality of object can be recognized within system 200 from the point of object ingestion through recognition in the field. The discussion of FIG. 2 also provides additional details of a process by which objects are ingested into the fast recognition ecosystem and then recognized in the field via mobile device 230. Although the example shown in FIG. 2 illustrates ingestion of buildings as modeled objects via image data, all objects are considered to fall within the scope of the process.

An object model server system can be configured to ingest new content information quickly based on object models. The object model server system can include modeling agent 220 that receives one or more of object model 225. Object model 225 could be programmatically constructed, procedurally constructed, scanned into modeling agent, or created through other techniques. As discussed previously, object model 225 can be constructed based on an active or passive scan of real-world physical objects. Object model 225 can represent any type of object in 2, 3, 4, or more dimensions of relevance. In the example shown, object model 225 comprises a wireframe rendering of a building. Modeling agents 225 are computing devices configured or programmed to leverage modeling utilities. Example modeling utilities can include Unity 3D® (see URL www.unity3d.com), OpenGL (see URL www.opengl.org), Maya® (see URL www.autodesk.com/products/autodesk-maya/overview) or other modeling technologies capable of configuring a computing device to digitally model objects.

Modeling agent 220 can execute one or more recognition algorithms 252 (e.g., recognition algorithms, feature detection, etc.) to generate derivable features. In the example shown in FIG. 2, the features are presented by small circles and squares. Still, it should be appreciated that the features can comprise location information, descriptors, or other data associated with the detected features. For example, modeling agent 220 can execute a feature detection algorithm, an edge detection algorithm, a corner detection algorithm, depth estimation determination algorithm, focal length estimation algorithm, camera intrinsics estimation algorithm, a character recognition algorithm, an image pattern detection algorithm, a symbol recognition algorithm, a biometric detection algorithm, an audio recognition algorithm, or other algorithms to a specific view of modeled object 225. To be clear, the features can be associated with each point-of-view from which object model 225 is analyzed. Each of recognition algorithm 252 yields one or more recognition features related to the specific view. In embodiments where object model 225 comprises a visual model, modeling agent 220 might execute implementations of SIFT, BRISK, and FAST just as one example. The features might include a set of SIFT features (e.g., locations, descriptors, etc.), a set of BRISK features, a set of FAST features, or other types of image features. In some embodiments, object model 225 could be generated from a real object where the object recognition features are derived from actual raw sensor data (e.g., an image from a camera, an audio track, etc.) representing the real-world object; a toy for example. In other embodiments, object model 225 could be generated by modeling agent 220 as a virtual object (e.g., a computer game rendered character, etc.) where the object recognition features are derived from data from simulated sensors or as rendered by modeling agent 220. A simulated sensor might include a virtual camera from whose point of view object model 225 is rendered.

An approach based on using real-world objects to create object models 225 has several advantages. Actively scanning a real-world object possibly using a laser, although expensive, generates a very accurate polygonal model of the object. Unfortunately, an active scanner fails to provide accurate image information. Passively scanning the real-world object possibly through a camera provides accurate real-world image data; however, object shape information derived from the image is less accurate than a laser scan. Combining the two sources of information provides an inexpensive accurate shape and accurate image of the real-world object.

An approach based on using virtual objects to create model also has advantages, although the virtual object might not reflect real-world circumstances. First, modeling agent 220 is able to generate numerous modeled positions or orientations of object model 225 quickly within a virtual environment without requiring manual data capture of a real-world object. Second, modeling agent 220 is not required to display object model 225. Rather, modeling agent 220 can function completely in data space or a virtual setting based on generated or rendered image data itself. Thus, generation of key frames 255 and associated information can be performed in batch, possibly distributed across numerous computing devices. Based on these first and second points, modeling agent 220 can quickly and autonomously generate recognition features. Third, modeling agent 220 can employ a virtual or simulated camera and adjust the radial position, focal length, or distance of the virtual camera from the object model 225, which allows for generating key frames 255 and related data from various distances as would happen in the real-world with a real, physical camera. Still, further as a fourth point, modeling agent 225 can adjust the parameters of the simulated virtual camera (e.g., pixel density, shutter speed, lens shape, focal length, focus, fidelity, field of view, etc.) or adjust the virtual environment parameters (e.g., light conditions, user skill, etc.). In view that modeling agent 220 can model many different dimensions associated with object model 225, one should appreciate that there are many degrees of freedom associated with modeled features associated with object model 225. For example, a camera can have six degrees of freedom (i.e., dimensions) relative to an object: X position, Y position, Z position, pitch, yaw, and roll. Additional recognition feature dimensions of relevance can include scale, translation, lighting, or other factors. Thus, modeling agent 220 is able to model virtually the vast recognition conditions under which an object might be recognized without requiring manual interaction.

In the example shown, modeling agent 220 constructs key frame 255. Key frame 255 comprises an image of object model 225 from a particular point of view and can be considered as a compact collection of the recognition features. It should be appreciated that key frame 255 could be a compact representation of the view, say a 64×64 pixel array from which recognition features could be re-derived. Although key frame 255 illustrates recognition features as being located on the image, one should appreciates that key frame 255 inherently encodes such features; and any other features even if they have not yet been identified. For example, Algorithm A and B might be SIFT and FAST. Still, key frame 255 could still have edges that could be detected via an edge detector that has not yet been executed on object model 225 or key frame 255. Thus, by storing key frame 255, the system can leverage new algorithms as they become available without requiring reconstruction of object models 225. The new algorithms can simply be executed on key frame 255 as desired to increase the object resolving power of disclosed techniques.

Key frame 255 can also be associated with a specific modeled feature of object model 225 that might be leveraged for tracking purposes. The modeled feature could be an observed edge feature for example. Note that the modeled feature in this example could also be a recognition feature. Still, key frame 255 can be bound with additional data or metadata about the circumstances under which key frame 255 was generated. Key frame 255 coupled with the additional information is referred to as key frame data. Example additional information could include a normal vector of the key frame relative to object model 225, camera distance from object model 225, lighting conditions, camera information, contextually attributes, or other types of data. This approach allows recognition engines to determine how recognition features map to tracking features very quickly.

Providing multiple key frames 255 for object model 225 can be quite advantageous. Rather than providing a complete representation of object model 225 or an entire object model database for object model 225 to mobile device 230, only relevant key frames 255 could be provided. This approach reduces bandwidth costs. For example, a corresponding object model database might have hundreds or thousands of indexed features, which could consume tens or even hundreds of megabytes. Instead, six of key frames 255 (i.e., ~100 KBs or a few MBs) could be sent to mobile device 230. In turn, mobile device 230 can generate the object model database from key frames 255 by executing the same algorithms used by modeling agent 220 to identify recognition features.

In view that the key frame data can include recognition features over the vast recognition conditions, the key frame data can also include confidence scores or metrics indicating the corresponding fidelity of the key frame data. As an example, consider a scenario where a person's face is modeled as object model 225. For multiple positions or orientations modeling agent 220 generates multiple sets of recognition features (e.g., SIFT descriptors, Canny edges, FAST corners, etc.) and key frames 255 at various modeled distances from the face (e.g., 0.5 meters, 1 meter, 2 meters, 4 meters, 10 meters, etc.). As the distance becomes greater, the modeled face subtends a smaller fraction of the virtual camera's field of view or in key frame 255, which in turn reduces the modeled image pixel count associated with the modeled face. The reduced pixel count would likely reduce the confidence in the ability of the system to match real-world recognition features to the key frame data. Interestingly, the disclosed approach also provides the ability to determine, at least to within a confidence level, a depth estimation determination of an object, a scale of the object, a translation, focal length estimation algorithm, camera intrinsics estimation algorithm, or even a skewing because the system has an understanding of how the modeled object appears to a camera at various orientations or positions based on the conditions used to generate key frames 255. Still further, the key frame data can also include context attributes (e.g., time, location, orientation, personal preferences, etc.) indicating contextual conditions under which the key frame bundles are relevant. In some embodiments, the recognition engine in the field (e.g., a cell phone) or modeling agent 220 can interpolate between key frame 255 poses to fill in gaps in key frame data as necessary. This approach allows for sending a small amount of key frame data to a recognition engine as discussed above, which can then build the necessary matching database or descriptors based on the key frame data.

The illustrated example in FIG. 2 presents a simple case where two feature-based algorithms are executed on object model 225 to obtain extracted features. The object features are illustrated as small circles and small squares where each feature corresponds to algorithms A and B, respectively. For example, circles might represent SIFT descriptors while squares might represent FAST corner feature points. One should note that features can be considered distinct, mathematically derived data objects that map to modeled features of the object model (e.g., vertices, edges, polygons, textures, normal vectors, audio samples, other recognition features, etc.) as represented by key frame 255. Thus, the collection of object features can be combined as with multiple key frames 255 from many different views or perspectives of object model 225. In a very real sense, the system has a pan-dimensional "understanding" of object model 225 because it is able to recall the object from nearly any perspective or under nearly any condition based on the extent of the generated key frame data.

Key frames 255 can be used in construction of object model database 260, which indexes recognition object models 260 as discussed previously. Object model database 260 can take on many different forms. In some embodiments, depending on the nature of the recognition features, recognition models 265 could comprises tree data structures. Each of object model 225 could have its own tree or multiple object models 255 could be bound together to form a single tree, perhaps grouped together based on classification of objects or context. Object model database 260 can be hosted on a remote server an accessed by mobile device 230 over a network (e.g., Internet, LAN, WAN, PAN, etc.). In other scenarios, object model database 260 could be hosted on mobile device 230. For example, mobile device 230 receive object model database 260 from the server. Additionally as new object models 225 are ingested, object model database 260 can be updated, possibly in real-time by the recognition engine, by inserting new recognition models 165 into the database or updating existing recognition model 165 with new key frame information.

In the field, mobile device 230 operating as a recognition engine captures a digital representation of scene 210. Mobile device 230 then derives recognition features 254 according to a recognition strategy as discussed above with reference to FIG. 1. Recognition features 254 are used to search through recognition models 265 in order to identify known objects. Object model database 260 can be configured to return object identifiers, which in turn can be used along with other contextual information to identify contextually relevant key frame bundles having links to content in content database 270. Mobile device 230 can then present the content to the user. For example, AR content can be presented to the user where the AR content is anchored to object features referenced in the key frame bundle. Additionally, the object can be tracked in real-time based on instructions within the key frame bundle.

Content information (e.g., links, URLs, image data, video data, audio data, augmented reality data, mask data, social media data, product data, text data, object data, object model data, game data, news data, multi-media data, etc.) can be stored in content database 270 as indexed by data bound to key frames 255. In some embodiments, content database 270 comprises object models, AR content, or other information directly or indirectly related to object model 225.

In additional embodiments, the content information can also include pointers (e.g., URLs, addresses, memory locations, etc.) to content. One should appreciate that content information can be indexed based on features from many key frames 255 related to a single object model 225. Once the content information and object models 225 are suitably ingested, objects corresponding to the object models 225 can be recognized in the filed by mobile device 230. Upon recognition, mobile device 230 can obtain contextually key frame bundles that can aid in additional recognition or tracking activities. The key frame bundles represent packages of data possibly sent to the cell phone in an XML, JSON, or other suitable format.

Recognizing many objects at the same time can include a recognition engine receiving a digital representation (e.g., image data, video data, audio data, biometric data, tactile data, etc.) of scene 210 comprising many objects. In the example shown, a cell phone (i.e., mobile device 230) has been configured or programmed to operate as a recognition engine per the discussion above and with respect to FIG. 1. The recognition engine can recognize at least some of the objects at least at a rate of one object per second, more preferably at least 10 objects per second, yet more preferably at least 100 objects per second, even more preferably 300 objects per second, or still more preferably at least 1000 objects per second. For example, an iPhone 5 cell phone can recognition many objects (e.g., 10 or more) within one sampling period for the digital representation. In an embodiment based where the digital representation includes video data, the sampling period might corresponding to the time it takes to display a single frame at a desired display frame rate.

The object recognition engine obtains one or more key frame bundles that could be considered contextually relevant to a current context of the recognition engine, perhaps based on device attributes (e.g., location, time, motion, etc.). It should be appreciated that the collection of key frame bundles could be associated with many different objects. Further, the key frame bundles delivered to the engine do not necessarily have to be all the key frame bundles for a target object. Rather, the delivered bundles could be a subset of bundles related to an object that are considered relevant. For example, if a person enters a mall, the device obtains key frame bundles bound to the location of the mall or stores within the mall. Each key frame bundle can include key frames corresponding to the modeled features, descriptors, recognition features, orientation, position, content links, scale, normal vector, or other information related to target objects or products. The data elements of the key frame bundles can be organized or arranged according to a nearest neighbor data structure (e.g., kd-tree, spill-tree, metric-tree, etc.) for quick look-up as discussed above.

As an example, consider a use case where the recognition engine in the field captures streaming video data as the digital representation. The recognition engine obtains a test image from the video stream where the test image could be considered a single frame of the video (e.g., every frame, every other frame, etc.). The engine then can extract one or more recognition features from the test image and use the recognition features to identify objects through the use of object model database 260. The object model database can return object identifiers, pointers to relevant key frame bundles, or other information. For example, the recognition features can be used to identify one or more bundles having key frames with similar descriptors via a kd-tree, spill-tree, or other kNN algorithm. In response, the recognition engine could obtain key frame bundles that are most contextually relevant to the observed objects in the current test image. Each key frame of the obtained key frame bundles represents a candidate that can be checked for similarity to the test image or a portion of the test image through a Hough transform by comparing the configuration of recognition features in the test image to the corresponding descriptors in the key frames by using low level matches to propose possible hypotheses for matched object. The engine can then perform a random sample consensus (RANSAC) verification to map the recognition features (e.g., 2D image descriptors) to corresponding higher dimensional features of the object (e.g., 3D scene, 3D objects, etc.) to reduce false positives. Content links in the key frame bundles can then be used, along with other information, to retrieve content from content database 270.

One should keep in mind that the recognition engine can further construct one or more queries based on the key frame data from the identified contextually relevant key frame bundles. One should note that key frame data can be a combination of different modalities of recognition algorithms where each different modality of recognition features (e.g., patterns, corners, etc.) can be used to determine how best to retrieve correspondingly indexed content information.

Content database 270 storing the content information can be searched quickly based on one or more techniques. In some embodiments, the database can search in parallel by submitting multiple sub-queries where each sub-query corresponds to one of the modalities of the recognition features. Such an approach is advantageous because the sub-query having the least search time will return a content information result set faster. Subsequently returned result sets can be used for validation or confirmation of the initial result set. For example, a multi-core processor could assign each core a search thread where each core looks up key frame bundles, content information, or other based on the queries.

The disclosed techniques give rise to multiple interesting capabilities. One example includes allowing a device, a cell phone for example, to track multiple recognized objects in real-time based on video data. As video data is captured, the device can track position or orientation of many objects relative to the device or to the background. Such capabilities are desirable during sporting events where multiple people or objects move quickly relative to each other. Tracked objects (e.g., players, balls, race cars, etc.) can be displayed along with related content information via an augmented reality overlay. The background can be tracked relative to the tracked objects through the use of vSLAM or other similar technologies.

In some embodiments, recognized objects can be tracked in video data through the key frame bundle information. The recognition engine leverages the recognition features from the test image to identify known objects based on relevant key frames 255. Once identify, the object information can be used to identify which key frame bundles have information that would be best for tracking the object. The key frames in the key frame bundles could aid the recognition engine in determining a pose of the camera relative to the object in the scene 210. The engine can further create an analysis window around the relevant recognition features in the test image based on the 3D points or normal vectors obtained from the information associated with the key frames 255. When a new test image is obtained (i.e., a new video frame), the engine searches in a radius about the previous location of the features within the new test image. Essentially, the engine searches for corresponding coarse level features from the original test image in the new test image. As corresponding features are found in the new test image, finer grain resolution analysis can be applied to establish 3D correspondences of model object features. The approach represents one possible recognition strategy that could be generated by the recognition engine. One should appreciate that the pose information aids in reducing search space for tracked features because the pose information in the key frame bundles indicates which features should or should not be visible. As an object moves and is tracked, the engine can predict based on the tracked movement which key frames 255 will likely become relevant in subsequent video frames. Based on experiments on an iPhone 5 over 300 features can be tracked at frame rate. Higher feature counts can be tracked, but a reduced bandwidth. Typically about 20 features are sufficient to recognize and track an object.

Another capability includes dynamically or contextually shifting recognition strategies. The recognition engine can determine a context based available sensor data (e.g., location, weather, proximity to others, etc.) and then execute a context-based filter to prioritize execution of the processing algorithms. Consider a scenario where a consumer has a pair of Google Glasses and is in shopping mall. The field of view of the glasses could cover thousands of recognizable objects, which could easily overwhelm the display of information to the consumer. When the consumer is walking around, perhaps the glasses use the location information to restrict the algorithms to only facial feature-based algorithms. When the consumer walks into a store, the recognition engine can shift the recognition strategy to product recognition based on SIFT. Further, when the consumer enters a food court, perhaps the recognition strategy shifts to symbol or logo-specific algorithms, possibly using edge detectors, that quickly identify food brands.

Yet another capability includes differentiating objects from each other and from the background. As a recognition engine recognizes objects, the engine can track the objects relative to each other even when the objects occlude each other. Consider an augmented reality gaming experience where real-world players move relative to each other and relative to virtual constructs. A game console operating as the recognition engine can observe the players, buildings, or other real-world objects as gaming objects. Once the objects are recognized, the recognition engine can obtain corresponding content information in the form of object models where the models can be used by the game console to differentiate the objects. The object models inform the game console the physical extent of each recognized object. Thus, the game console is able to differentiate the recognized objects from other constructs even based on partial key frame information.

Another possible use case includes combining the disclosed capabilities with toys. Electronic toys can be outfitted with a recognition engine capable of converting 2D image content into a full understanding of a 3D environment. A small car or robot could navigate around a home environment by monitoring position or location of recognized objects in the home. Alternatively, the toy could follow a child as the toy would recognize the child's form or face. Still further, a tablet or cell phone can be configured to recognize many toys. For example, a Disney® princess play set could include many figures or items, all of which can be known to the device. As a child moves the objects relative to each other, the associated content can be obtained based on the relative positions thereby allowing the child to discover new content by unlocking the content through play.

One should also appreciate that the disclosed recognition engines can operate in an environment that has non-visual triggers, perhaps while the person's cell phone is in their pocket. During such a quiescent state, the cell phone might monitor ambient non-visual sensor data (e.g., sound, accelerometry, GPS, temperature, etc.) periodically. During this time, the cell phone recognition engine can derive one or more contexts from the ambient data; perhaps a daily commute context based on GPS location and time of day, a birthday context based on audio detection of dinner conversation, a sporting context based on audio detection of noise level, or other context. The recognition engine can instantiate the contexts from the non-visual recognition features derived from the ambient data, then request key frame bundles based on the non-visual contexts. In response, the cell phone can obtain one or more key frame bundles appropriate for the context, then build a recognition strategy from the context and key frame bundle information. In the case of a daily commute context, the key frame bundles could include key frames for known vehicles or even license plates in case that driver would like to record evidence of an accident should an accident occur. In the case of a birthday context, the recognition engine could download key frame bundles associated products in nearby stores or that are age relevant to a person under discussion. Within the sporting context, the recognition engine could obtain key frame bundles that include recognition descriptors associated with the athletes.

In some consumer related use-cases, obtaining key frame bundles or construction of recognition strategies can be triggered by sound, music, songs, jingles or other non-visual information. To expand further on the on the example of a cell phone operating in a quiescent state in a person's pocket or purse, the cell phone can recognize a song or jingle while a person peruses a store. The recognition features of derived from the song possible coupled with location information (e.g., GPS coordinates, Wi-Fi triangulation, compressive sensing, etc.) can trigger the pre-caching of key frame bundles as discussed above. Further, the information can trigger structuring of the recognition strategy, perhaps by even by aisle.

Vehicles, robots, or other autonomous machines can also leverage the disclosed techniques. Consider semi-automated vehicle (e.g., drone, Martian probe, etc) or a driverless automobile. As the vehicle, or robot for that matter, moves through an area, then key frame bundles can be pre-cached within the vehicle's memory as a function of location or position information. Such an approach is considered advantageous because such devices will only be required to search through contextually relevant information rather than large, massive datasets, which in turn allows the vehicles to be much more responsive to their contextual circumstances. More specifically, a driverless vehicle in a parking lot would likely require a recognition strategy and key frame bundles that are sensitive to humans as distinguished from background objects (e.g., buildings, lamp posts, other vehicles, etc.). However, the driverless vehicle on the highway would likely require a recognition strategy and key frame bundles that allow the vehicle to be more responsive to other moving vehicles and to quickly track moving objects.

One of the major advantages of the disclosed approach of providing key frame bundles coupled with executing contextual recognition strategies is that it allows devices having limited computing or memory resources to nearly instantaneously respond to the presence of multiple objects at the same time. If a computing device had infinite resources (e.g., CPU bandwidth, memory capacity, memory access, processing time, etc.), then a device obviously would not require advanced techniques for reducing latency in responding to objects. However, the in the world of mobile device (e.g., cell phone, tablets, toys, hand held game systems, PDAs, phablets, vehicles, medical devices, UAVs, etc.) that have limited resources, the computing resources required to recognize 3D objects quickly should also be balanced against battery power consumption. In view that the disclosed techniques are able to take into account contextual information, a device's power consumption rate can factor into which key frame bundles are prioritized for delivery or even which algorithms are used to reduce battery consumption. For example, key frame bundles can be prioritized by their size so that only small, relevant bundles are sent first to reduce to the number of wireless transmissions necessary to populate the recognition engines. Larger, less relevant bundles might be filtered out to extend battery life. As an additional example, the recognition strategies can be constructed to utilize a minimum number of cores in a multi-core processor or to use algorithms that have reduced memory transfers to reduce power consumption.

The disclosed techniques are of special interest in embodiments where objects do not necessarily exist before observation. Consider a gaming scenario where a computer game is configured to generate objects procedurally in real-time. An example of such a game includes No Man's Sky™ under development by Hello Games™ (See URL www.no-mans-sky.com). In such a case it is impossible to known a priori the nature of the object. However, the disclosed techniques can be leveraged to generate recognition features during objects instantiation in real-time. These recognition features can then be fed into the known object model database in real-time so that a gaming system could then observe the objects, recognize the objects, and interact with the objects based on the content information. This approach could be considered a just-it-time recognition system.

Another aspect of the inventive subject matter relates to protocols through which a client interacts with a recognition service. The protocols can be sensitive to context, especially with respect to relevant data modalities. From a client side perspective (e.g., recognition engine, cell phone, etc.), each modality can be compared for saliency content. For example, how effective the modality is in the current context to distinguish or recognize objects. As an example, if the device determines that an audio channel is not particularly informative, the audio such information does not necessarily have to be sent to a back end recognition services. Additionally, if a device is not moving, then there is no need to use gyroscopic or accelerometery information. Still further, if a video scene is not change, rather than sending or processing a video clip, the client device could just send a single frame representative of the clip.

From the server side perspective, the recognition strategy can be re-prioritized according to context information obtained from the client. Perhaps camera facing information can be used along with position information so that the recognition strategy focuses first on the type of objects in view. Thus, geo-location, position, or orientation information provides device environment cues to modify recognition likelihood priors to known objects in the database. The server could then send subjects of the database to the client based on locations or the modality of interest. In such a case, the server could send only modality-relevant data to the client. Still further the server can recommend to the client how to modify or adjust its own recognition strategy. For example, the server might indicate that one or more of the following techniques should be executed first: 2D markers, 3D in hue space, edge-based recognition, edge detection plus scene detection, edge detection plus 3D hue space, etc.

The inventive subject matter is also considered to include numerous variations beyond those discussed above. For example, Table 1 lists a possible set of claims from an object ingestion system perspective.

TABLE 1

Possible System Claims

| Claim Number | Claim |
|---|---|
| 1. | A model recognition system comprising:<br>an object model database configured to store recognition models related to object models and object information indexed by recognition features according to the recognition models, each object model including modeled features of an object; and<br>a object model server coupled with the object model database and configured to:<br>generate a plurality of key frame bundles having key frame data, each key frame bundle corresponding to one of the objects;<br>provide access to the plurality of key frame bundles to a user device;<br>submit a query derived from a target key frame bundle identified by the user device to a content database;<br>obtain content information related to the at least one object model from the content database that satisfies the query; and<br>provide the content information to a computing device. |
| 2. | The system of claim 1, wherein the key frame bundle comprises an image. |
| 3. | The system of claim 1, wherein the key frame bundle comprises at least one recognition feature. |
| 4. | The system of claim 3, wherein the at least one recognition features comprises an image descriptor. |
| 5. | The system of claim 1, wherein the query comprises at least one of the recognition features. |
| 6. | The system of claim 1, wherein the object models stored within the object model database are indexed according to the recognition features. |
| 7. | The system of claim 1, wherein in the recognition features comprises algorithm features derivable from digital representation processing algorithms. |
| 8. | The system of claim 7, wherein in the algorithms include at least one of the following types of algorithms: a feature detection algorithm, an edge detection algorithm, a corner detection algorithm, depth estimation determination algorithm, focal length estimation algorithm, camera intrinsics estimation algorithm, a character recognition algorithm, an image pattern detection algorithm, a symbol recognition algorithm, a biometric detection algorithm, a curve detection algorithm, and an audio recognition algorithm |
| 9. | The system of claim 1, wherein the content information comprises multi-media data. |
| 10. | The system of claim 1, wherein the content information comprise at least one of the following: image data, video data, audio data, augmented reality data, mask data, social media data, product data, text data, object data, object model data, game data, and news data. |
| 11. | The system of claim 1, further comprising a mobile device operating as the recognition engine. |
| 12. | The system of claim 11, wherein the mobile device comprises at least one of the following: a cell phone, a smart phone, a tablet, a vehicle, a medical device, and a game console. |
| 13. | The system of claim 1, wherein the key frame bundle includes at least of the following: a 3D normal vector, a 3D coordinate, an estimated focal length, a lighting condition, and a deformation. |

Further the inventive subject matter is considered to include method of a device recognizing objects at high rates per unit time. Table 2 lists a set of possible claims directed to an method of a device quickly recognizing objects.

TABLE 2

Possible Object Ingestion System

| Claim Number | Claim |
|---|---|
| 1. | A method of recognizing a plurality objects comprising:<br>receiving, by a recognition engine, a digital representation of the plurality objects;<br>recognizing at least some of the objects from the digital representation at a rate of X objects per Y unit of time by:<br>deriving, by the recognition engine, a set of recognition features by executing algorithms on the digital representation; |

TABLE 2-continued

Possible Object Ingestion System

| Claim Number | Claim |
|---|---|
| | constructing, by the recognition engine, a key frame query based on the set of recognition features; and identifying, by the recognition engine, at least some of the objects by searching for content information related to object models and indexed by key frame data that satisfy the key frame query; providing the at least some of the content information to a computing device; and wherein X/Y is at least 1 object per second. |
| 2. | The method of claim 1, wherein X/Y is at least 10 objects per second. |
| 3. | The method of claim 2, wherein X/Y is at least 100 objects per second. |
| 4. | The method of claim 3, wherein X/Y is at least 300 objects per second. |
| 5. | The method of claim 4, wherein X/Y is at least 1000 objects per second. |
| 6. | The method of claim 1, wherein X/Y is at least 10 objects per digital representation sample time. |
| 7. | The method of claim 6, wherein the digital representation sample time is determined as a function of a display frame rate. |
| 8. | The method of claim 1, further comprising programming a mobile device to operate as the recognition engine. |
| 9. | The method of claim 1, wherein the digital representation comprises at least one of the following types of data: image data, video data, audio data, and biometric data. |
| 10. | The method of claim 1, wherein the object models comprises 3D models. |
| 11. | The method of claim 1, determining, by the recognition engine, a recognition strategy based on the digital representation, the recognition strategy comprising an algorithm application rules set governing application of the algorithms to the digital representation. |
| 12. | The method of claim 11, wherein the step of deriving a set of recognition features includes executing the algorithms on the digital representation according to the algorithm application rules set. |
| 13. | The method of claim 11, wherein the algorithm application rules set depends on at least one of the following: a time, a location, an orientation, a context, a position, a user, a license agreement, a digital representation attribute, a frame rate, a hierarchy, and an ontology. |
| 14. | The apparatus of claim 1, wherein the content information comprises multi-media data. |
| 15. | The apparatus of claim 1, wherein the content information comprise at least one of the following: image data, video data, audio data, augmented reality data, mask data, social media data, product data, text data, object data, object model data, game data, and news data. |

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An apparatus comprising:
   at least one sensor configured to obtain a digital representation of a plurality of objects; and
   a recognition engine coupled with the at least one sensor and configured to:
   obtain access to an object model database storing recognition models of known object models, the recognition models having features derived from key frames of known object models;
   determine a recognition strategy based on the digital representation, the recognition strategy comprising an algorithm application rules set governing application of a plurality of algorithms to the digital representation;
   generate at least one recognition feature by executing the plurality of algorithms on the digital representation according to the algorithm application rules set;
   identify a target modeled object in the object model database where the corresponding recognition model has features similar to the at least one recognition feature;
   identify a target key frame bundle having a content link based on the target modeled object;
   retrieve content information associated with a plurality of object models corresponding to at least some of the plurality objects based on the content link of the target key frame bundle; and
   render at least some of the content information on a display screen.

2. The apparatus of claim 1, wherein the known object models comprise at least three dimensional models.

3. The apparatus of claim 1, wherein the content information comprises an object model mask.

4. The apparatus of claim 3, wherein the content information comprises a green screen mask.

5. The apparatus of claim 1, wherein the plurality of algorithms include at least one of the following types of algorithmic components: a feature detection algorithm, an edge detection algorithm, a corner detection algorithm, depth estimation determination algorithm, focal length estimation algorithm, camera intrinsics estimation algorithm, a character recognition algorithm, an image pattern detection algorithm, a symbol recognition algorithm, a biometric detection algorithm, and an audio recognition algorithm.

6. The apparatus of claim 1, wherein the plurality of algorithms include at least one of the following algorithms: SIFT, FAST, DAISY, FREAK, SURF, BRISK, ASR, and OCR.

7. The apparatus of claim 1, wherein the target key frame bundle comprises object tracking features.

8. The apparatus of claim 1, the recognition engine is further configured to generate the recognition features substantially in real-time with respect to receiving the digital representation.

9. The apparatus of claim 1, wherein the digital representation includes at least one of the following types of data: image data, text data, audio data, video data, and biometric data.

10. The apparatus of claim 1, wherein the recognition engine is configured to identify at least X of the object models per Y unit of time, where X/Y is at least 1 object model per second.

11. The apparatus of claim 10, wherein the X/Y is at least 10 object models per second.

12. The apparatus of claim 11, wherein the X/Y is at least 300 objects per second.

13. The apparatus of claim 1, wherein the recognition engine is further configured to generate the recognition features and identify the at least one target modeled object within one sampling period of the digital representation.

14. The apparatus of claim 13, the sampling period comprises a time period no greater than a single image frame rendering time.

15. The apparatus of claim 14, wherein the single image frame rendering time is no greater than approximately $1/24^{th}$ of a second.

16. The apparatus of claim 1, further comprising a mobile device incorporating the recognition engine.

17. The apparatus of claim 16, wherein the mobile device further incorporates the sensor.

18. The apparatus of claim 17, wherein the sensor is selected from the group consisting of: a GPS sensor, a hall probe, a camera, an RFID reader, a near field radio, a microphone, a biometric sensor, a touch screen, an accelerometer, a magnetometer, a gyroscope, a spectrometer, a strain gauge, a stress gauge, a pulse oximeter, a seisometer, a galvanometer, a Radar sensor, a LIDAR sensor, an infrared sensor, a flow meter, an anemometer, a Geiger counter, a scintillator, a barometer, and a piezoelectric sensor.

19. The apparatus of claim 16, wherein the mobile devices comprises at least one of the following: a cell phone, a tablet, a kiosk, an appliance, a vehicle, and a game console.

20. The apparatus of claim 1, wherein the content information comprises multi-media data.

21. The apparatus of claim 1, wherein the content information comprise at least one of the following: image data, video data, audio data, augmented reality data, mask data, social media data, product data, text data, object data, object model data, game data, and news data.

22. The apparatus of claim 1, wherein the recognition engine is further configured to obtain access to the object model database by construction the object model database from the plurality of key frames.

23. The apparatus of claim 1, wherein the recognition engine is further configured to obtain access to the object model database by receiving the object model database from a server.

24. The apparatus of claim 1, wherein the recognition engine is further configured to obtain access to the object model database over a network.

25. The apparatus of claim 1, wherein the recognition engine is further configured to update the object model database based on new key frames.

* * * * *